United States Patent
Lilley, Jr.

(10) Patent No.: US 6,475,189 B1
(45) Date of Patent: Nov. 5, 2002

(54) APPARATUS AND METHOD FOR A SELF-BLUNTING SAFETY CATHETER

(75) Inventor: Thomas F. Lilley, Jr., Simsbury, CT (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/469,742

(22) Filed: Dec. 21, 1999

(51) Int. Cl.$^7$ .............................................. A61M 5/178
(52) U.S. Cl. .............................. 604/164.01; 604/164.05
(58) Field of Search ........................ 604/164.01, 164.05, 604/168.01, 158, 170.01, 198; 606/213; 600/567; 128/751

(56) References Cited

U.S. PATENT DOCUMENTS

| | | | |
|---|---|---|---|
| 4,627,841 A | | 12/1986 | Dorr |
| 4,713,057 A | | 12/1987 | Huttner, et al. |
| 5,172,700 A | * | 12/1992 | Bencini et al. ............. 128/751 |
| 5,246,426 A | * | 9/1993 | Lewis et al. ........... 604/168.01 |
| 5,312,345 A | | 5/1994 | Cole |
| 5,743,882 A | * | 4/1998 | Luther ................... 604/164.05 |
| 5,893,845 A | * | 4/1999 | Newby et al. ............... 604/198 |
| 5,951,520 A | * | 9/1999 | Burzynski et al. ..... 604/170.01 |
| 6,050,976 A | * | 4/2000 | Thorne et al. ......... 604/184.01 |
| 6,149,607 A | * | 11/2000 | Simpson et al. ............ 600/567 |
| 6,171,281 B1 | * | 1/2001 | Zhang ................... 604/164.01 |
| 6,197,042 B1 | * | 3/2001 | Ginn et al. .................. 606/213 |
| 6,213,978 B1 | * | 4/2001 | Voyten .................. 604/164.01 |
| 6,270,480 B1 | * | 8/2001 | Dorr et al. ................... 604/158 |

FOREIGN PATENT DOCUMENTS

| | | |
|---|---|---|
| EP | 1110576 | 6/2001 |
| WO | WO94/11050 | 5/1994 |
| WO | WO98/26821 | 6/1998 |
| WO | WO98/57689 | 12/1998 |

* cited by examiner

Primary Examiner—Teresa Walberg
Assistant Examiner—Leonid M Fastovsky
(74) Attorney, Agent, or Firm—Blakely, Sokoloff, Taylor & Zafman LLP

(57) ABSTRACT

A catheter unit having a needle, an actuator body, and an elongated blunting member coupled to a flash chamber and to carriage. The blunting member is disposed coaxially within the bore of the needle. The blunting member is capable of moving from a proximal to distal position when the distal ends of at least one of the longitudinal members is pressed on the outer surface of the distal end causing the longitudinal member to advance which in turn causes the longitudinal member to press against a member causing the blunting member to advance from a proximal position to a distal position.

18 Claims, 8 Drawing Sheets

APPARATUS AND METHOD FOR A SELF-BLUNTING SAFETY CATHETER

BACKGROUND OF THE INVENTION

1. Field of the Invention

The invention relates generally to intravascular devices and more specifically to a blunting apparatus.

2. Description of Related Art

Intravascular assemblies such as catheter assemblies are generally used for passing fluids between a device such as a syringe or a drip to or from body lumens such as veins or arteries, or other internal target sites. A catheter assembly usually includes a hub, a catheter, and a needle. An eyelet ring is typically inserted into the catheter. The catheter, together with the eyelet ring, is then inserted into an opening in the nose of the hub and is secured to the hub by press fitting the eyelet ring within the nose of the hub. A needle is then inserted into the catheter. A sharp tip of the needle is used for piercing a body lumen so that access may be gained into the body lumen by the catheter and the needle. Once the catheter and the needle are located within the body lumen, the needle is removed. A syringe or a pipe of a drip is then attached to the hub so that fluids may be passed through the hub and the catheter between the drip or the syringe and the body lumen. The hub is typically made of materials that provide sufficient rigidity thereto and the catheter is usually made of a material which is flexible.

One of the potential problems associated with a catheter involves the sharp tip of the introducer needle. After a health care worker has used a catheter on a patient, the sharpened tip of the needle that has bodily fluids from the patient may cause harm to another person by the sharpened tip coming in contact with the skin of another. Accordingly, there is a need to provide catheters that reduce the likelihood of a catheter unit causing harm to another person such as a health care workers.

SUMMARY OF THE INVENTION

A catheter unit comprising a needle, an actuator body, and an elongated blunting member coupled to a flash chamber and to a safety member. The blunting member is disposed coaxially within the bore of the needle. Additional features, embodiments, and benefits will be evident in view of the figures and detailed description presented herein.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION OF THE INVENTION

Methods and apparatuses are disclosed wherein an intravascular assembly such as a catheter unit is modeled such that the blunting apparatus of the catheter can be advanced or retracted based upon the actions of the user of the catheter. In one embodiment, an actuator body that generally comprises a first and a second longitudinal member wherein pressure is applied against the proximal portion of one member of the actuator body of a catheter such that at least one end such as the distal end of the longitudinal member of the actuator body moves away from the blunting member in an outward direction releasing a hub of the catheter. In another embodiment of the invention, a user may compress a first longitudinal member and a second longitudinal member at the proximal ends of the longitudinal members. This results in the distal end of the first longitudinal member and the distal end of the second longitudinal member releasing the hub of the catheter.

Figure 1:
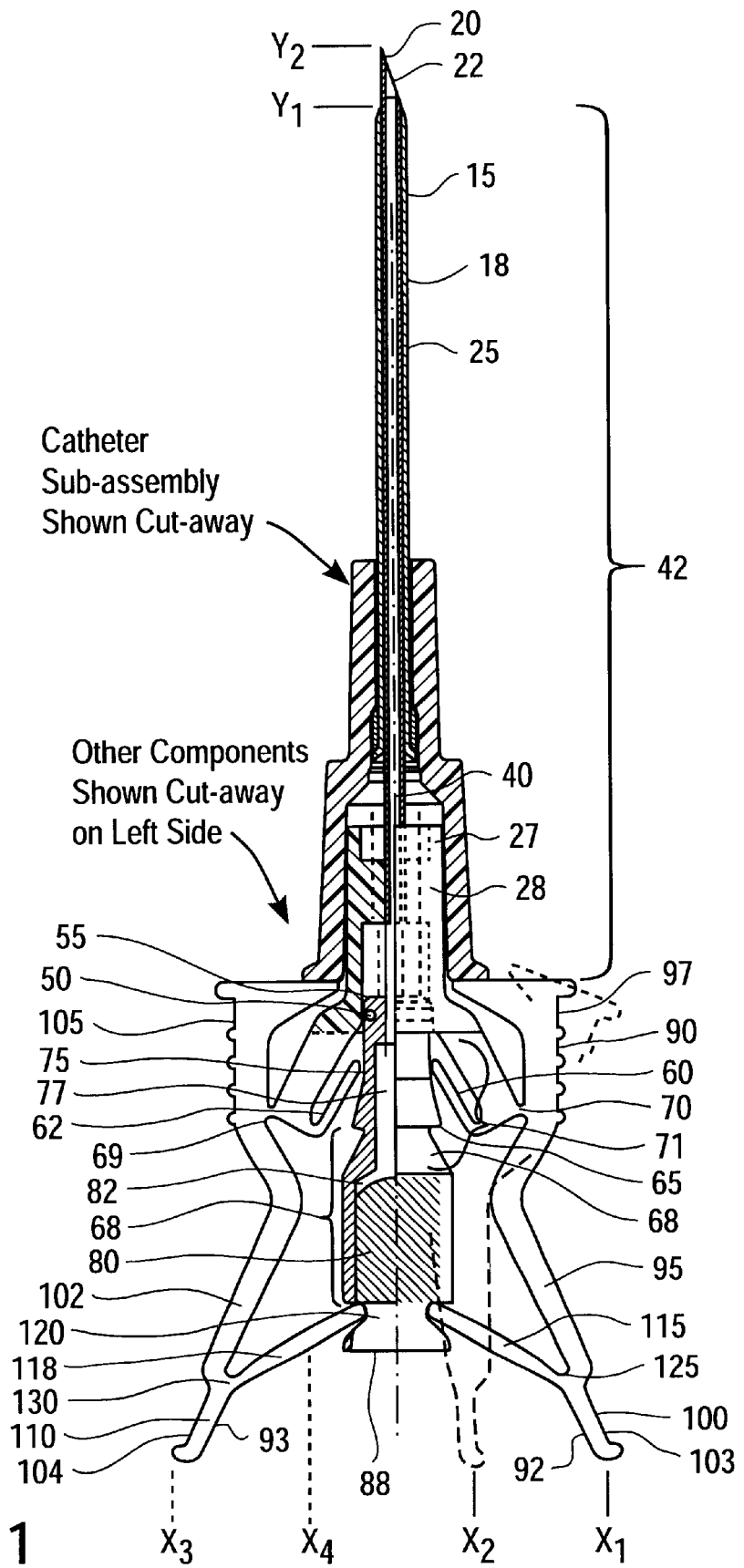
FIG. 1 is a perspective view of an intravascular assembly such as a catheter of one embodiment of the invention.

FIG. 1 shows one embodiment of the invention. Needle 15 extends outwardly from a nose 27. Needle 15 is formed of material such as stainless steel hypotubing and has a beveled or otherwise sharpened distal tip 20. A hollow bore 22 extends longitudinally through needle 15.

A transparent flash chamber housing 75 of flash member 71 is formed on the proximal end of the elongated blunting member 40. A gap exits between carriage 55 and nose 27 which allows blood or other bodily fluids to enter. A hollow flash chamber bore 77 extends longitudinally through the proximal flash chamber housing 75. The longitudinal flash chamber bore 77 has a cylindrical proximal inner wall of substantially continuous diameter. There is a continuous fluid path from hollow inner bore 77 and hollow bore 22 of needle 15 with and connected to hollow bore 22 of needle 15. Coupled to the flash chamber is carriage 55 with blunting member 40. Blunting member 40 is secured at the proximal end of carriage 55.

Needle blunting apparatus 42 comprises an elongated blunting member 40 and carriage 55 used to secure blunting member 40. Elongated blunting member 40 is preferably formed of rigid material such as stainless steel hypotubing. Blunting apparatus 42 has an outer diameter which is slightly smaller than the inner diameter of hollow bore 22 of needle 15. This allows the blunting member to easily slide into hollow bore 22 of needle 15. A blunt distal tip is formed at the end of blunting member 40.

Blunting member 40 is formed on or otherwise associated with the blunting apparatus 42 to anchor or hold the blunting member in its respective "non-blunting" and "blunting" positions. O-ring 50 is used as a sliding seal between carriage 55 and the nose 27 of the hub 28, or actuator body. A seal can also be achieved with a flexible lip seal that is an integral feature of carriage 55 or with sufficiently small clearance between carriage 55 and needle boss/actuator body. A variety of methods may be used to secure blunting member 40 to carriage 55. For example, blunting member 40 may be glued or attached to the inner portion of carriage 55 at the proximal end. Carriage 55 with the blunting member thereto is coupled to lock shoulder 65 and to first lock finger 60 and second lock finger 62. Lock shoulder 65 is cylindrical and tapers as lock shoulder 65 extends to the distal end. Lock shoulder 65 is coupled to member 68 at the proximal end of the catheter unit.

Member 68 is cylindrical in shape and narrows at a distal end. Member 68 serves the function of containing porous member (80) or stopper that substantially prevents bodily fluids from escaping the catheter. A porous member (80) generally fits securely within chamber 82. Cap-like member 88 is coupled to chamber 82 at the proximal end of chamber 82. A neck resides between cap-like member 88 and chamber 82. Neck 120 is coupled to hook portion 115 of first longitudinal member 95 and hook portion 118 of second longitudinal member 102.

FIG. 1 shows blunting member 40 in a distal position $Y_2$. Needle 15 and blunting apparatus 42 are initially disposed in a coaxially nested arrangement as shown in FIG. 1 wherein needle 15 extends coaxially through lumen 18 of catheter 25. In the retracted position $Y_1$ blunting member 40 does not extend through a portion of bore 22 of hollow bore of the needle 15.

As stated above, actuator body 90 generally comprises two longitudinal members such as first longitudinal member 95 and second longitudinal member 102. Each longitudinal member has a proximal end and a distal end. When pressure is applied to at least one of the proximal ends of one of the longitudinal members, the distal end of that longitudinal member moves up and away from the blunting apparatus. It will be appreciated that the actuator body may be characterized by more than two longitudinal members.

Blunting member 40 is adaptable to move from a proximal position $Y_1$ to a distal position $Y_2$. In the proximal position $Y_1$, blunting member 40 is retracted. Therefore, the distal member of blunting member 40 does not extend beyond the distal end of needle 15.

Figure 2:
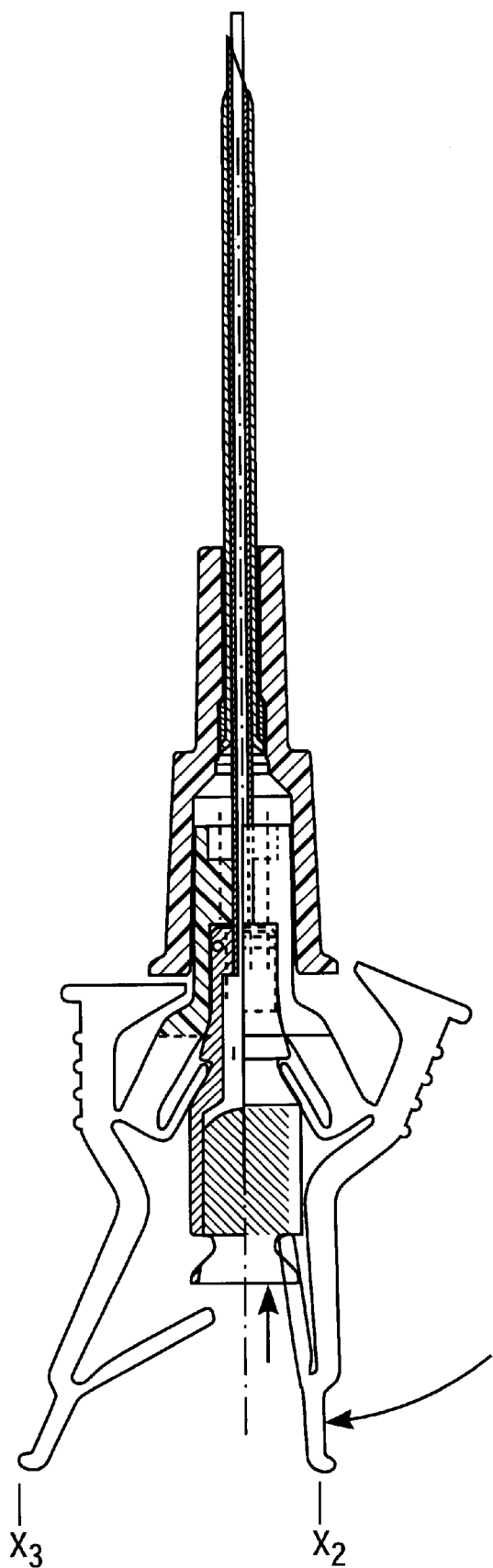
FIG. 2 is the same device as in FIG. 1 except it shows the intravascular assembly of FIG. 1 in which the proximal end of the first longitudinal member moves from an extended position to a retracted position.

Blunting member 40 advances to distal position $Y_2$ as shown in FIG. 2. In order to advance to distal position $Y_2$, second end 100 of first longitudinal member 95 or second end 110 of second longitudinal member 102 or both second ends of the longitudinal member (95, 102) must be compressed or gently squeezed on the outside portion of the second ends of the longitudinal member by the user. A gentle squeezing or pressing action causes the actuation of blunting member 40. Specifically, the second end of the second longitudinal member 102 or the first longitudinal member 95 is compressed, wherein the second end bends inwardly about the proximal hinge of that longitudinal member. This causes the hook of that longitudinal member to press against neck 120. When the hook of the longitudinal member presses against neck 120, member 68 presses against lock shoulder 65 resulting in lock shoulder 65 advancing to a position above lock fingers 60 and 62. Lock fingers 60 and 62 stay in position while lock shoulder 65 advances. Lock shoulder 65 impacts carriage 55. Carriage 55 holds blunting member 40 in place and blunting member 40 advances from position $Y_1$, to position $Y_2$. Once the blunting member 40 advances to the proximal position $Y_2$, blunting member 40 locks in place with a distinct audible and tactile click. This clicking noise serves to indicate to a user such as a health care worker that the distal position has been reached. It will be appreciated that carriage 55 may be formed or configured in a variety of ways without departing from its intended functions, including the function of providing a means of holding blunting member 40 in a secure manner and facilitating movement of blunting apparatus 42.

Figure 3:
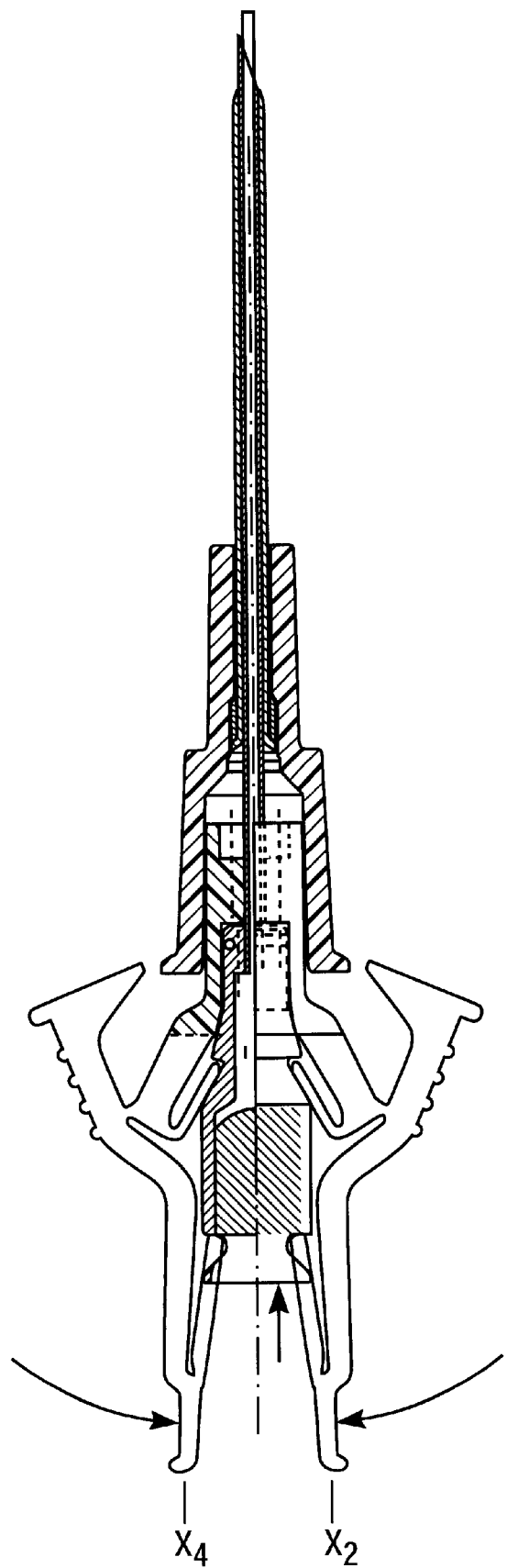
FIG. 3 shows the same device as in FIG. 1 wherein both longitudinal members of the actuator body are compressed.

Second end 100 of first longitudinal member 95 moves from position $X_1$ to position $X_2$ about first distal hinge 70 when second end 100 of first longitudinal member 95 compressed by the user. Alternatively, second longitudinal member 102 may be moved from position $X_3$ to position $X_4$ about the second distal hinge 69. Hinges (125, 130) allow hook portions (115, 118) of the first longitudinal member and the second longitudinal member (95, 102) to have inward motion similar to first longitudinal member and second longitudinal member (95, 102) where connected to first longitudinal member and second longitudinal member (95, 102) when first longitudinal member and the second longitudinal member (95, 102) are moved inward, and hook portions (115, 118) have an upward motion where coupled to member 68. Hinges (69, 70) may serve as pivots allowing the first ends of first and second longitudinal members (97, 105) to move, turn, or rotate about the hinges (69, 70). It will be appreciated that a ball and socket joint may be used instead of a hinge. FIG. 2 shows first longitudinal member 95 moving from position $X_1$ to position $X_2$. By doing so, blunting member 40 is advanced from proximal position $Y_1$ to distal position $Y_2$. FIG. 3 shows both longitudinal members undergoing compression at second ends (100, 110) resulting in blunting member 40 secured in blunting apparatus 42 advancing from proximal position $Y_1$ to distal position $Y_2$.

Second ends (100, 110) have inner (92, 93) and an outer surface (103, 104). The outer surfaces (103, 104) allow a user to hold and compress second ends (100, 110).

Figure 4:
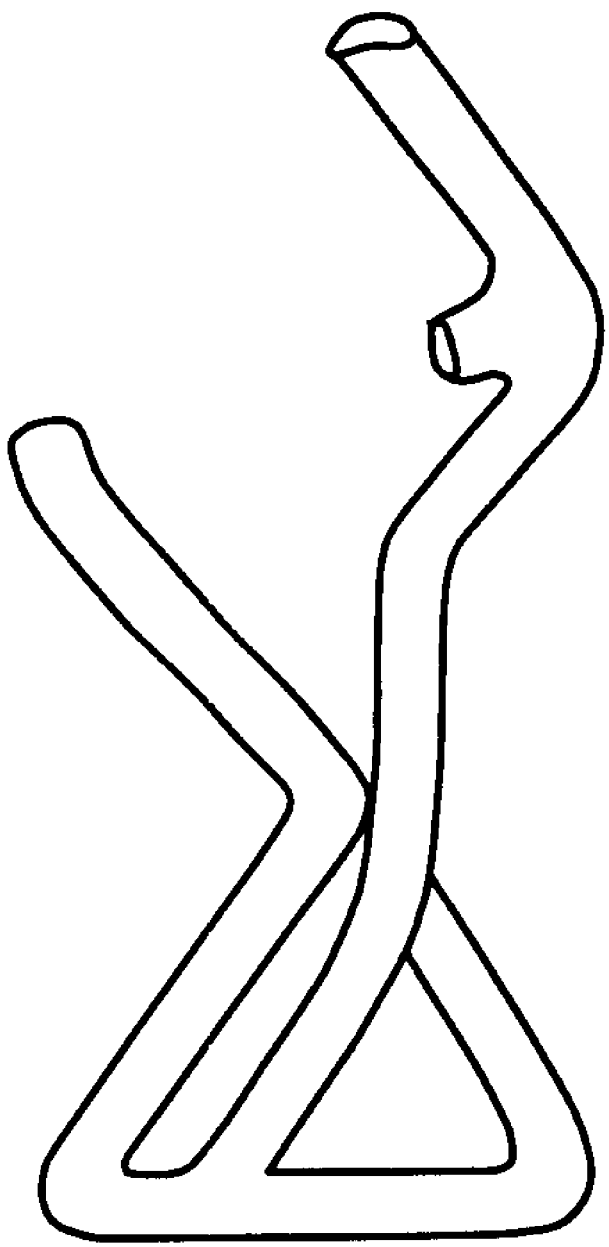
FIG. 4 shows a proximal hinge about which a longitudinal member pivots of one embodiment of the invention.

FIG. 4 shows an enlarged view of one embodiment of a proximal hinge used in one of the longitudinal members which provides a means for moving blunting apparatus 42 from a proximal position $Y_1$, to a distal position $Y_2$.

Figure 5:
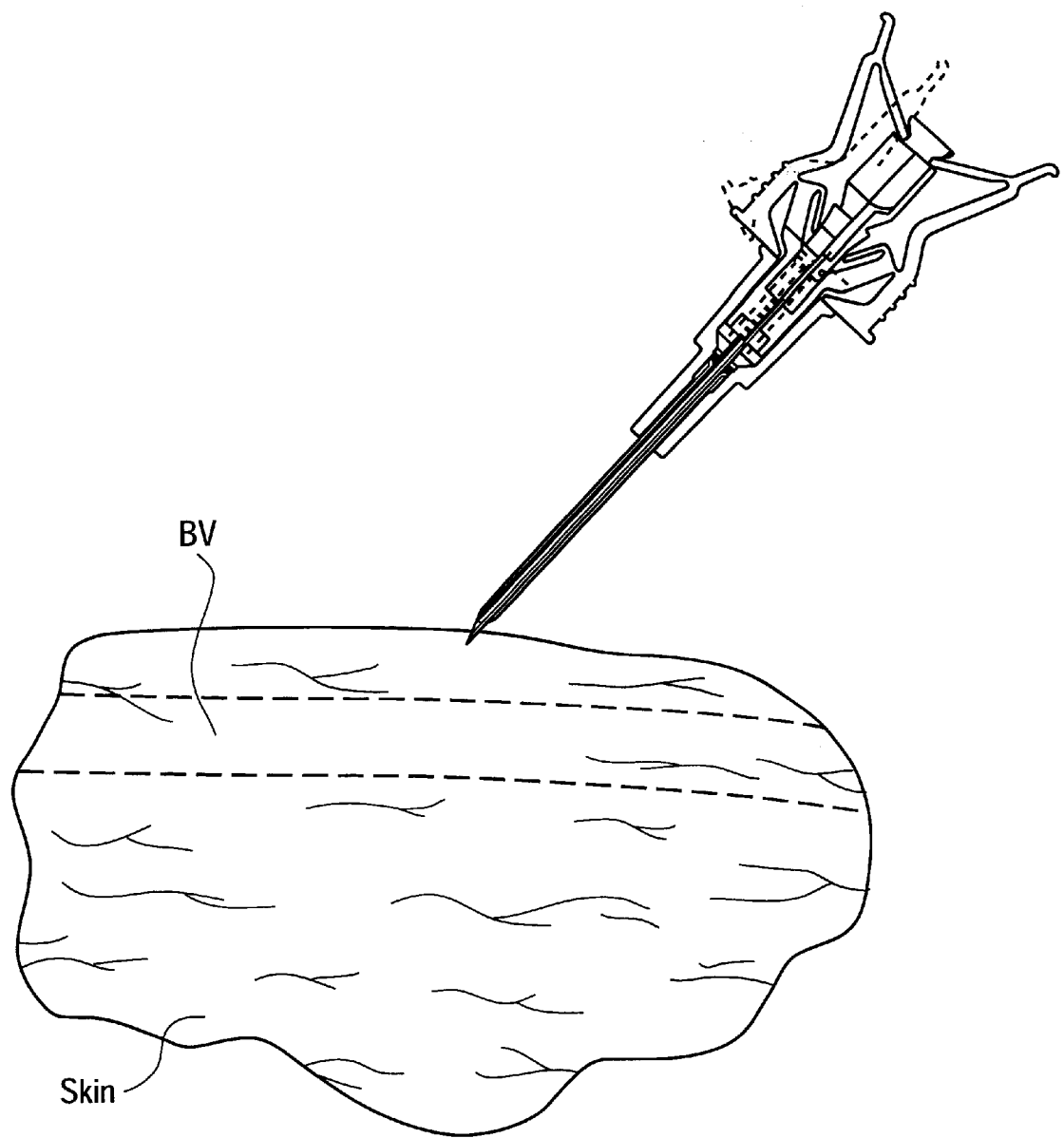
FIG. 5 shows an intravascular assembly of one embodiment of the invention approaching a patient's skin.
Figure 6:
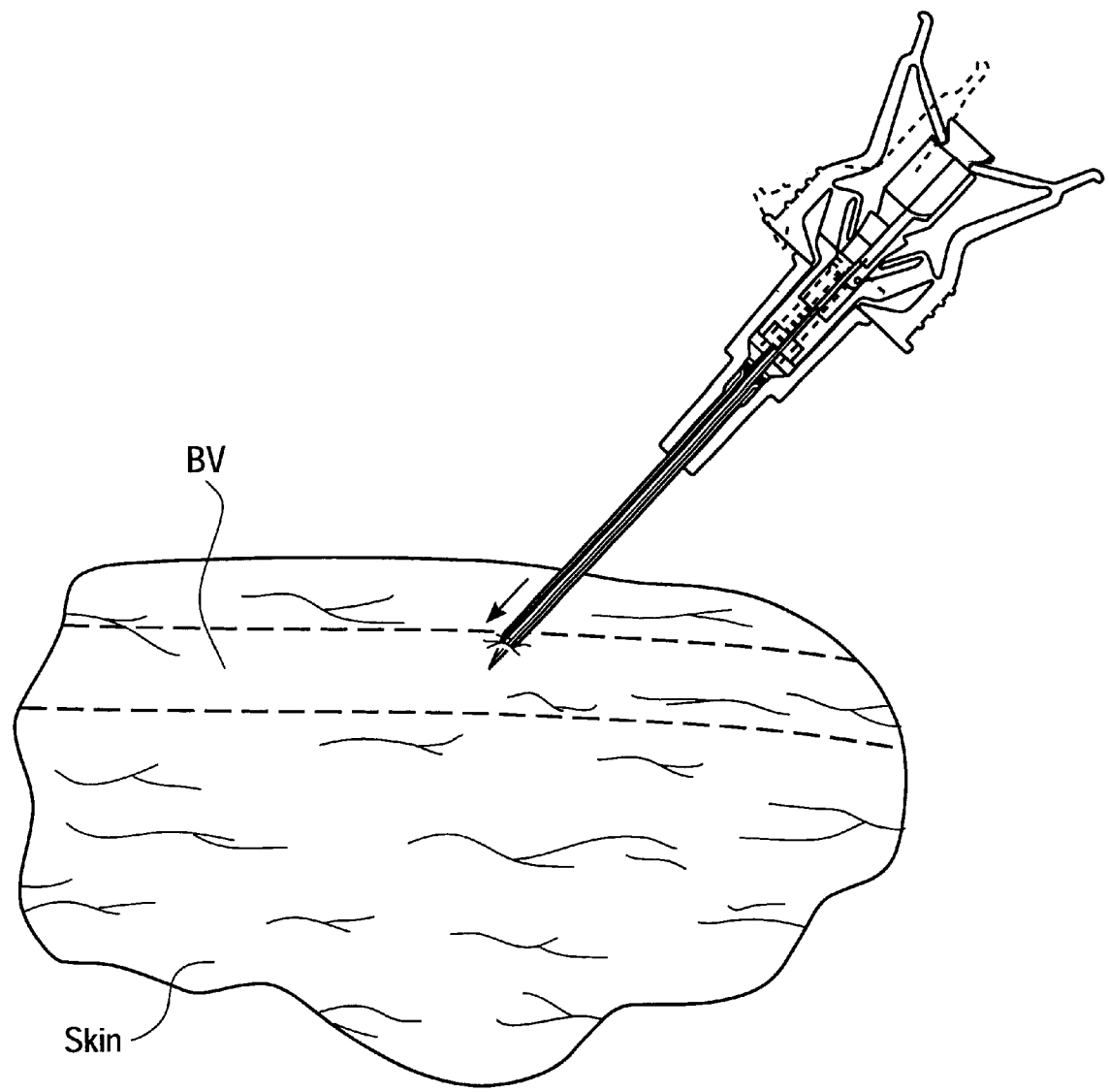
FIG. 6 shows the percutaneously insertion of a needle of the intravascular assembly into the blood vessel of a patient.
Figure 7:
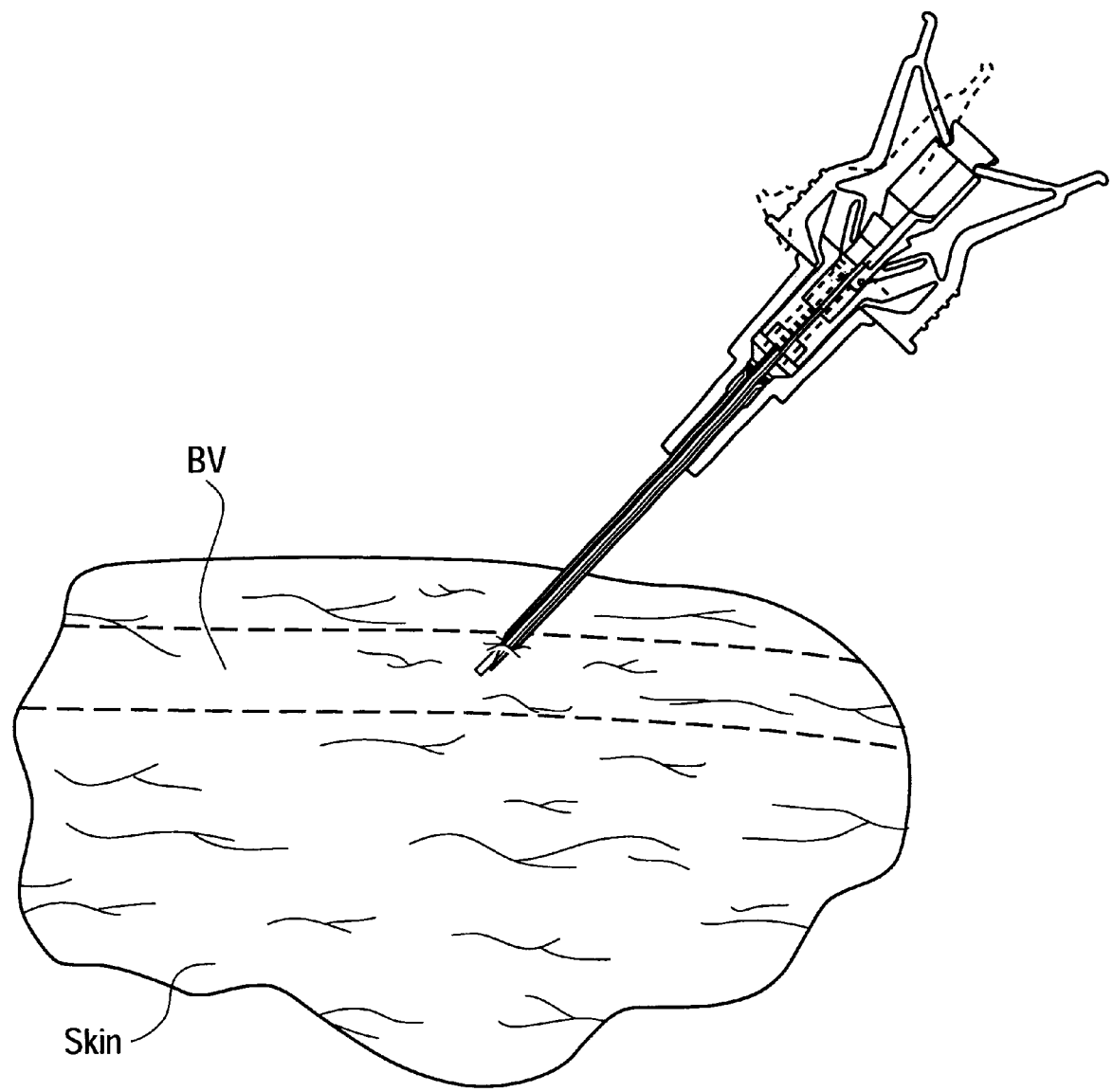
FIG. 7 shows the blunting member of the assembly having moved from a proximal position to a distal position wherein the blunting member extends beyond the distal tip of the needle of the intravascular assembly.

FIGS. 5 through 7 show one mode of using one of the embodiments of the invention. FIG. 5 shows needle 15 prior to entering the skin of a patient. A blood vessel is beneath the skin. The blunting apparatus 42 is initially retracted to its "non-blunting" position or proximal position shown in FIG. 4. In FIG. 6, distal tip 20 of needle 15 pierces the skin or is percutaneously inserted into a blood vessel BV, as shown in FIG. 6. FIG. 7 shows the distal tip of blunting member 40 extends by a distance of $Y_2$ beyond the beveled or sharpened distal tip 20 of needle 15. Needle 15 is thereafter incapable of puncturing or harming the user to other individuals who may come into contact with used needle 15.

Figure 8:
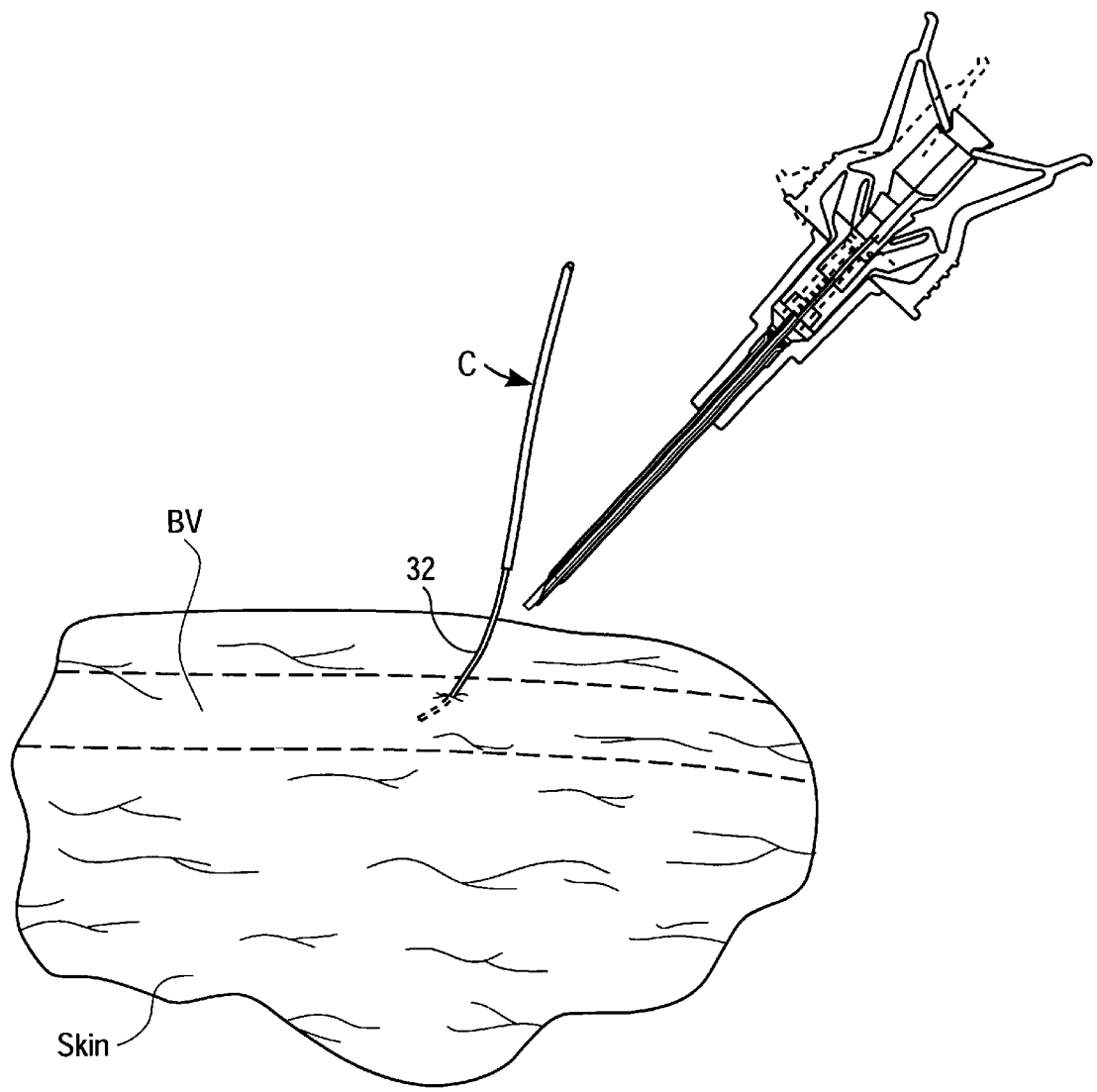
FIG. 8 shows that after the needle and the blunting apparatus of the assembly have been removed, and a catheter is about to be inserted into the introducer of an intravascular assembly.

FIG. 8 shows needle 15 and blunting apparatus 42 have been removed. FIG. 8 also shows a tubular catheter C advanced through introducer 32. Thereafter, introducer 32 is withdrawn leaving catheter C within the blood vessel BV.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A catheter unit comprising:
   a needle;
   a hub;
   an actuator body, the actuator body having a first member and a second member, wherein at least one of the members is coupled to the hub; and
   a blunting member coupled to a flash chamber and to a barrier member, the blunting member being disposed coaxially within the bore of the needle and to be actuated by the actuator.

2. The catheter unit of claim 1, wherein the actuator body further comprises:
   a first member having a first end and a second end, the second end is coupled to a first distal hinge and to a first proximal hinge, the first end has a first finger grip; and
   a first proximal hinge.

3. The catheter unit of claim 1, wherein the actuator body further comprises:
   a second member having a first end and a second end, the second end is coupled to a first distal hinge and to a first proximal hinge, the first end has a first finger grip; and
   a first proximal hinge.

4. The catheter unit of claim 3, further comprises:
   the hub is coupled to the first member and the second member.

5. The catheter unit of claim 3, wherein the second end of the first longitudinal member has an outer surface and an inner surface and the second end of the second longitudinal member has a first surface and a second surface.

6. The catheter unit of claim 5, wherein the hub is released from the first member and the second member by pressing the outer surface of the second end of the first longitudinal member.

7. The catheter unit of claim 5, wherein the hub is released from the second longitudinal member by pressing the outer surface of the second end of the second longitudinal member.

8. The catheter unit of claim 4, wherein the hub is related by the first member and the second member by the first and second arm moving outwardly in a radial direction.

9. The catheter unit of claim 1, wherein the flash chamber has a proximal end and a distal end and a porous member is attached to the distal end of the flash chamber.

10. The catheter unit of claim 2, wherein the porous member is removable.

11. The catheter of claim 6, wherein the blunt advances to a distal position.

12. An intravascular assembly, the assembly comprising:
   a tubular introducer sheath having a proximal end, a distal end and a hollow lumen extending longitudinally therethrough;
   a needle having a sharpened distal tip and a hollow bore extending longitudinally therethrough, the needle being initially disposed coaxially within the lumen of the introducer sheath such that the sharpened distal tip of the needle protrudes out of and beyond the distal end of the introducer sheath; and
   an elongated blunting member;
   and an actuator body to actuate the blunting member.

13. The intravascular assembly of claim 12, wherein the actuator body comprises:
   a first member and a second member, the first member having a proximal end which forms a lever and distal end, the distal end has one surface which is grooved; and
   a second member having a proximal end which forms a lever and a distal end, the distal end is grooved.

14. The intravascular assembly of claim 13, wherein the proximal end of the first member transitions to a rotatable member to a stem of the blunting member.

15. The intravascular assembly of claim 13, wherein the proximal end of the second member transitions to a rotatable member to a stem of the blunting member.

16. The intravascular assembly of claim 13, wherein the proximal end of the first member is coupled to a turnable member and to the stem of the blunting member.

17. The intravascular assembly of claim 13, wherein the proximal end of the second member is coupled to a turnable member and to the stem of the blunting member.

18. A method of moving a blunt member in a catheter comprising:
   gripping an actuator body, the actuator body is coupled to a blunting member, the blunting member coaxially nestled into a needle;
   squeezing a first lever of the actuator body, wherein the first lever causes a first longitudinal member to move, the first longitudinal member is coupled to a first proximal hinge to a stem of the blunting member;
   squeezing a second lever, wherein the second lever causes a second longitudinal member to move, the second longitudinal member is coupled to a second proximal hinge and to the stem of the blunting member; and
   moving the blunting member to a distal position.

* * * * *

UNITED STATES PATENT AND TRADEMARK OFFICE
CERTIFICATE OF CORRECTION

PATENT NO. : 6,475,189 B1
DATED : November 5, 2002
INVENTOR(S) : Thomas F. Lilley, Jr.

Page 1 of 1

It is certified that error appears in the above-identified patent and that said Letters Patent is hereby corrected as shown below:

Column 4,
Lines 62-63, please delete "the members" and replace with -- the first member and the second member --.
Line 66, please delete "within the bore of the needle and to be" and replace with -- within a bore of the needle and adapted to be --.
Line 67, please delete "actuator" and replace with -- actuator body --.

Column 5,
Line 3, prior to "a first member" please insert -- a first distal hinge and a first proximal hinge, --.
Line 3, please delete "a first member" and replace with -- the first member –.
Lines 4-5, please delete "to a first distal hinge and to a first proximal hinge" and replace with -- to the first distal hinge and to the first proximal hinge --.
Line 5-6, please delete ";and a first proximal hinge".
Line 9, prior to "a second member" please insert -- a first distal hinge and a first proximal hinge, --.
Line 9, please delete "a second member' and replace with -- the second member --.
Lines 10-11, please delete "to a first distal hinge and to a first proximal hinge" and replace with -- to the first distal hinge and to the first proximal hinge --.
Lines 11-12, please delete ";and a first proximal hinge".

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,475,189 B1
DATED         : November 5, 2002
INVENTOR(S)   : Thomas F. Lilley, Jr.

It is certified that error appears in the above-identified patent and that said Letters Patent is hereby corrected as shown below:

Column 5,
Line 18, please delete "first longitudinal member" and replace with -- first member --.
Lines 19-20, please delete "second longitundinal member" and replace with -- second member --.
Line 20, please delete "a first surface and a second surface" and replace with -- an outer surface and an inner surface --.
Lines 23-24, please delete "first longitudinal member" and replace with -- first member --.
Lines 29-31, please delete "related by the first member and the second member by the first and second arm" and replace with -- released from the first member and the second member by first and second arms --.
Line 35, please delete "claim 2" and replace with -- claim 9 --.
Line 37, please delete "catheter of claim 6, wherein the blunt" and replace with -- catheter of claim 6, wherein the blunting member --.

Column 6,
Line 11, please delete "and distal" and replace with -- and having a distal --.
Line 14, please delete "a second" and replace with -- the second --.
Line 15, please delete "and a distal end" and replace with -- and having a distal end --.
Lines 18 and 21, please delete "member to a stem" and replace with -- member and to a stem --.
Lines 25 and 28, please delete "to the stem" and replace with -- to a stem --.
Line 37, please delete "hinge to a stem" and replace with -- hinge and to a stem --.

Signed and Sealed this

Seventh Day of September, 2004

JON W. DUDAS
*Director of the United States Patent and Trademark Office*